(12) United States Patent
Chouinard et al.

(10) Patent No.: US 11,801,388 B2
(45) Date of Patent: Oct. 31, 2023

(54) ROBUST ADAPTIVE BRAIN STIMULATION

(71) Applicant: Medtronic, Inc., Minneapolis, MN (US)

(72) Inventors: Thomas L. Chouinard, Maple Grove, MN (US); Scott R. Stanslaski, Shoreview, MN (US); Timothy R. Abraham, Lino Lakes, MN (US); Robert S. Raike, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 143 days.

(21) Appl. No.: 17/541,939

(22) Filed: Dec. 3, 2021

(65) Prior Publication Data
US 2022/0176134 A1    Jun. 9, 2022

Related U.S. Application Data

(60) Provisional application No. 63/199,069, filed on Dec. 4, 2020.

(51) Int. Cl.
*A61N 1/37* (2006.01)
*A61N 1/372* (2006.01)
*A61N 1/36* (2006.01)
*A61N 1/05* (2006.01)

(52) U.S. Cl.
CPC ....... *A61N 1/37235* (2013.01); *A61N 1/0534* (2013.01); *A61N 1/3615* (2013.01); *A61N 1/36082* (2013.01); *A61N 1/36135* (2013.01); *A61N 1/36175* (2013.01)

(58) Field of Classification Search
CPC .............. A61N 1/0534; A61N 1/36082; A61N 1/36135; A61N 1/36139; A61N 1/3615; A61N 1/36175; A61N 1/37235; A61N 1/37247
See application file for complete search history.

(56) References Cited

U.S. PATENT DOCUMENTS

| | | | |
|---|---|---|---|
| 5,683,422 | A | 11/1997 | Rise |
| 5,716,377 | A | 2/1998 | Rise et al. |
| 10,471,264 | B2 | 11/2019 | Bourget et al. |
| 2009/0082829 | A1 | 3/2009 | Panken et al. |

*Primary Examiner* — Amanda K Hulbert
(74) *Attorney, Agent, or Firm* — Patterson Thuente IP

(57) ABSTRACT

Systems and methods that automatically adjust, or adapt, stimulation waveforms delivered to brain structures. Closed loop system embodiments can automatically be reconfigured into a more suitable closed loop control system in response to measures of control system performance. Measures can be internal performance characteristics of the adaptive control system or external inputs provided by another subsystem. As these measures change in time, the robust adaptive system changes in response.

26 Claims, 9 Drawing Sheets

ROBUST ADAPTIVE BRAIN STIMULATION

CROSS-REFERENCE TO RELATED APPLICATIONS

This application claims the benefit of U.S. Provisional Application Ser. No. 63/199,069, filed Dec. 4, 2020, the disclosure of which is hereby incorporated by reference in its entirety.

FIELD

The present technology is generally related to medical devices and, more particularly, medical devices that deliver adaptive brain stimulation therapy.

BACKGROUND

Patients with neurodegenerative diseases or trauma like cerebral infarct or spinal cord injury can have a variety of movement and muscle control problems, like resting, postural, intention or action tremor; dystonia (improper muscle tone, myoclonus); spasticity (undesirable movements, or muscle co-contraction); dyskinesia (poorly executed movements) or involuntary movements like ballismus, choreiform movements and torticollis (inappropriate movements or limb control). Many of these problems can be called hyperkinesia. Although they can be chronic, or worse, progressive, they also may have times of relative remission. Such problems are found, at certain stages, for patients with Parkinson's disease, multiple sclerosis, cerebral palsy, secondary to deafferentation pain, post stroke, post apoplexy or anoxia, post head or spinal trauma, post poisoning, cerebellar disease, etc. Dyskinesia also may result from long term usage of L-dopa, or Levodopa, for Parkinson's patients, or other drugs.

Medical devices that provide deep brain stimulation (DBS) of certain brain structures can alleviate, diminish, or completely stop symptoms of the aforementioned diseases or traumas. Traditionally, DBS therapy was provided as a continuous train of pulses. However, more recent advances have adapted or regulated the stimulation delivered to the brain, for example, by getting physiological feedback and adjusting the therapy, often against threshold values.

However, patient states in a disease can change week-to-week or day-to-day or even by hour as medications or circadian rhythms change symptoms. Further, diseases can progress over time. Moreover, it can be difficult to set appropriate forward-looking threshold values at any given point in time (e.g. at the clinic). And, changing those thresholds often requires an additional clinic visit. Accordingly, a constant therapy or even threshold-adjusted therapy is not always appropriate. Further, a one-size-fits-all algorithm or set of algorithms that DBS devices implement may not be optimal.

Therefore, there is a need to adapt the adaptive DBS therapies themselves.

SUMMARY

The techniques of this disclosure generally relate to embodiments that automatically adjust, or adapt, stimulation waveforms delivered to brain structures. Adaptive brain stimulation systems include a measurement and an actuation system. For example, a local field potential sensor, and/or movement sensor is used in a measurement system, and in coordination, an actuation system can include a stimulation waveform adjustment to a parameter such as amplitude, pulse width, rate, location (electrode configuration) or some combination therein. The measurement system provides real-time feedback to the actuation system, as in the classically defined closed-loop control system. Embodiments described herein include an adaptive brain stimulation system, which itself can adapt. Moreover, closed loop system embodiments can automatically be re-configured into a more suitable closed loop control system in response to measures of control system performance. Measures can include internal performance characteristics of the adaptive control system (e.g. dwell time/entropy in a particular state, actuator saturation, actuator oscillation/stability), or external inputs provided by another subsystem (e.g. poor symptom control, undesired side effects). As these measures change in time, the robust adaptive system changes in response.

In an embodiment, the disclosure describes an adaptive deep brain stimulation system comprising at least one processor and memory operably coupled to the at least one processor, a measurement subsystem including a plurality of sensing contacts, and measurement subsystem instructions that, when executed on the at least one processor, cause the processor to implement a first signal classification algorithm using one or more of the plurality of sensing contacts to generate a first plurality of signals of interest, an actuation subsystem including a plurality of stimulation contacts and actuation subsystem instructions that, when executed on the at least one processor, cause the processor to provide therapy on one or more of the plurality of stimulation contacts by one or more actuators according to a first control policy and a first control parameter, a reconfiguration subsystem including reconfiguration subsystem instructions that, when executed on the at least one processor, cause the processor to determine at least one performance measure related to the measurement subsystem or the actuation subsystem, detect a change in performance of the at least one performance measure against a performance threshold, and based on the detecting, generate updated measurement subsystem instructions, wherein the updated measurement subsystem instructions includes a second signal classification algorithm or a second plurality of signals of interest, or generate updated actuation subsystem instructions, wherein the updated actuation subsystem instructions includes a second control policy or a second control parameter, and store at least one of the updated measurement subsystem instructions or the updated actuation subsystem instructions in the memory, wherein the updated measurement subsystem instructions or the updated actuation subsystem instructions, when executed on the at least one processor, cause the processor to provide an updated therapy on the one or more of the plurality of stimulation contacts.

In an embodiment, the disclosure describes a method for adapting an adaptive deep brain stimulation system including at least one processor and memory operably coupled to the at least one processor, a measurement subsystem including a plurality of sensing contacts, and measurement subsystem instructions that, when executed on the at least one processor, cause the processor to implement a first signal classification algorithm using one or more of the plurality of sensing contacts to generate a first plurality of signals of interest, and an actuation subsystem including a plurality of stimulation contacts, and actuation subsystem instructions that, when executed on the at least one processor, cause the processor to provide therapy on one or more of the plurality of stimulation contacts by one or more actuators according to a first control policy and a first control parameter, the method comprising determining at least one performance measure related to the measurement subsystem or the actuation subsystem, detecting a change in performance of the at least one performance measure against a performance threshold, and based on the detecting, generating updated measurement subsystem instructions, wherein the updated measurement subsystem instructions includes a second signal classification algorithm or a second plurality of signals of interest, or generating updated actuation subsystem instructions, wherein the updated actuation subsystem instructions includes a second control policy or a second control parameter, storing at least one of the updated measurement subsystem instructions or the updated actuation subsystem instructions in the memory, wherein the updated measurement subsystem instructions or the updated actuation subsystem instructions, when executed on the at least one processor, cause the processor to provide an updated therapy on the one or more of the plurality of stimulation contacts.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
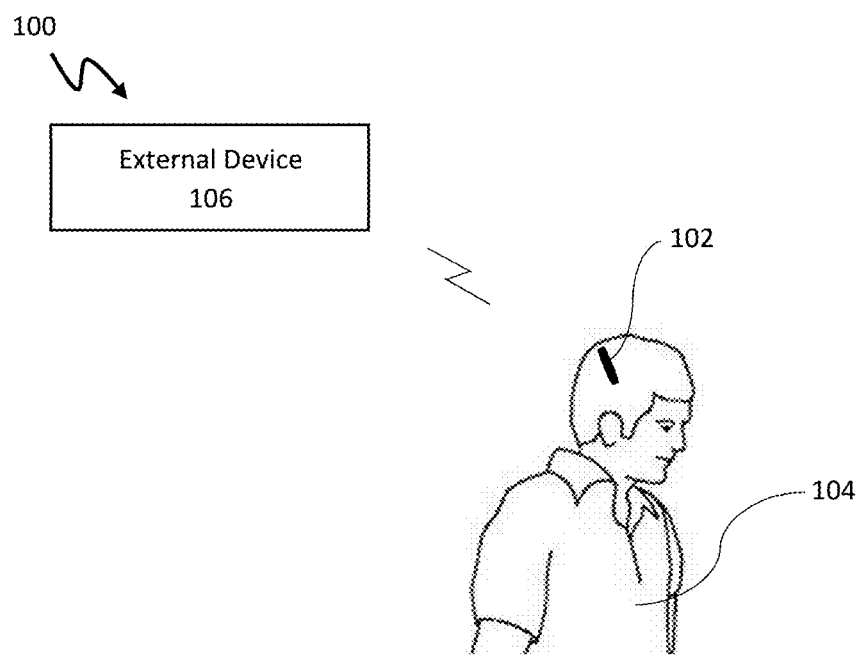
FIG. 1 is a conceptual diagram illustrating an example system that provides robust adaptive brain stimulation, according to an embodiment.

Referring to FIG. 1, a conceptual diagram illustrating an example system 100 that provides robust adaptive brain stimulation is depicted, according to an embodiment. In an embodiment, system 100 comprises an implantable medical device (IMD) 102 for a patient 104.

IMD 102 delivers neurostimulation therapy to patient 104 at a target tissue site. For example, one or more leads may extend from IMD 102 to the brain of patient 104, and IMD 102 may deliver deep brain stimulation (DBS) therapy to patient 104 to, for example, treat the aforementioned neurodegenerative diseases or traumas.

IMD 102 is configured to deliver therapy according to one or more programs or control policies. A control policy includes one or more parameters that define an aspect of the therapy delivered by the medical device according to that control policy. For example, a control policy that controls delivery of stimulation by IMD 102 in the form of pulses may define a voltage or current pulse amplitude, a pulse width, a pulse rate, an electrode configuration or field shape, or a schedule or pattern for stimulation pulses delivered by IMD 102 according to that control policy. Further, each of the leads includes electrodes, and the parameters for a control policy that controls delivery of stimulation therapy by IMD 102 can include information identifying which electrodes have been selected for delivery of pulses according to the program, and the polarities of the selected electrodes, i.e., the electrode configuration for the control policy. Control policies that control delivery of other therapies by IMD 102 can include other parameters, as required by the particular policy.

Optionally, in an embodiment, as depicted, system 100 further comprises an external device 106. External device 106 is communicatively coupled to IMD 102 via wireless communication. In embodiments, external device 106 can be a device for inputting information relating to patient 104, receiving information from IMD 102, and updating IMD 102 according to the robust adaptive algorithms and methods described herein.

Figure 2:
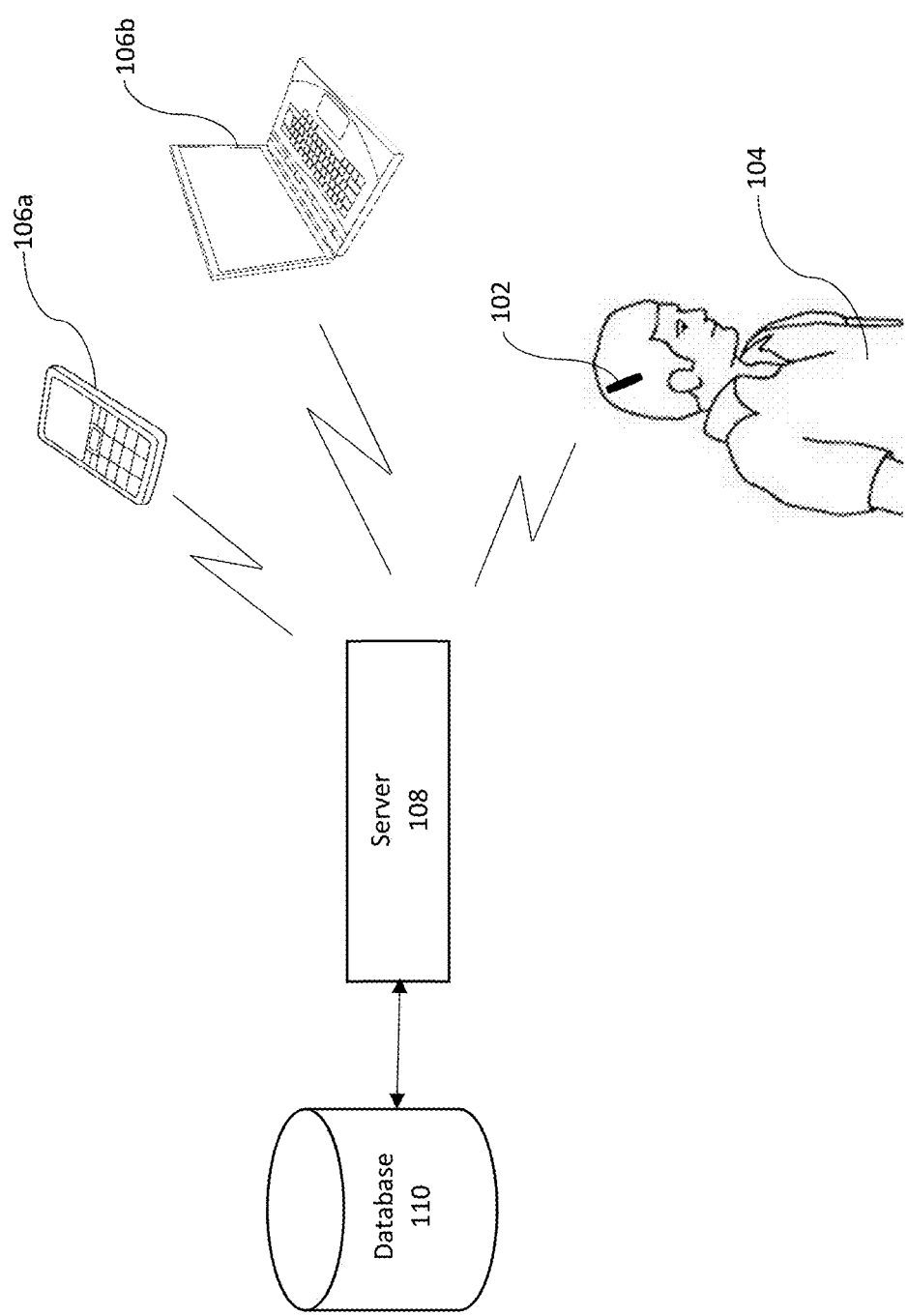
FIG. 2 is a conceptual diagram illustrating an example system that provides robust adaptive brain stimulation, according to an embodiment.

Referring also to FIG. 2, a conceptual diagram illustrating an example system that provides robust adaptive brain stimulation is depicted, according to an embodiment.

As depicted, external devices 106a and 106b are further illustrated as a handheld computing device and a laptop computing device, but can further be a key fob or a wristwatch, smart phone, computer workstation, or networked computing device, and the like.

Embodiments of systems can further include a server 108 and/or a database 110, as illustrated.

Server 108 can include one or more servers in a cloud computing environment. Server 108 can be configured to communicate with external devices 106a and/or 106b, and/or or IMD 102 via wireless communication. In embodiments, server 108 can be co-located with external devices 106a and/or 106b, or located elsewhere, such as in a cloud computing data center or medical clinic.

Database 110 is configured to store data related to system 100, including IMD 102 and/or external device 106 data. In embodiments, database 110 can be integrated as part of server 108, or be standalone such that server 110 and/or external device 106a and 106b can be communicatively coupled to database 110.

Figure 3:
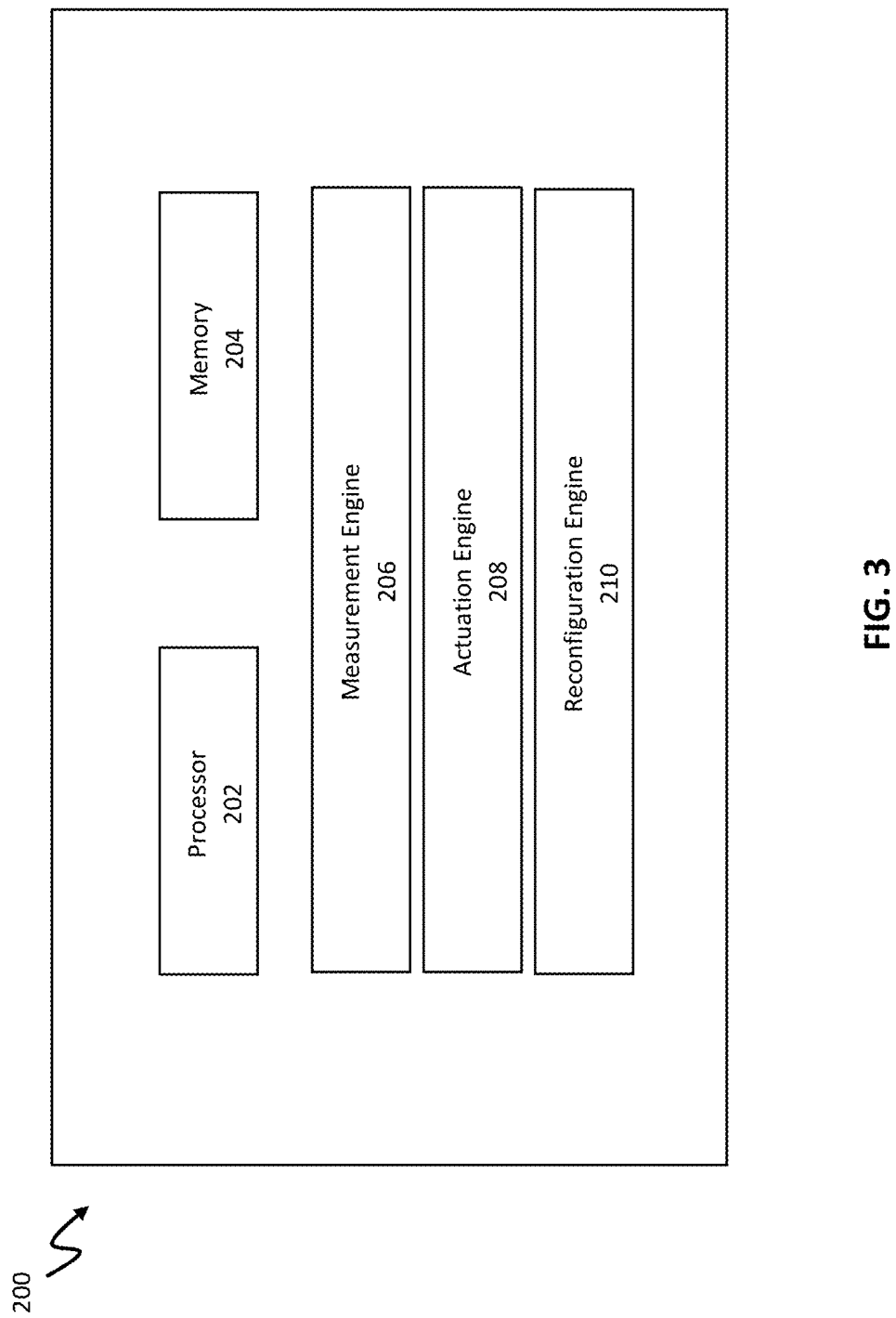
FIG. 3 is a block diagram of a system, including various engines, that provides robust adaptive brain stimulation, according to an embodiment.

Referring to FIG. 3, a block diagram of a system 200, including various engines, that provides robust adaptive brain stimulation is depicted, according to an embodiment.

System 200 generally comprises at least one processor 202 and memory 204 for implementing engines measurement engine 206, actuation engine 208, and reconfiguration engine 210.

The various engines or tools are constructed, programmed, configured, or otherwise adapted, to autonomously carry out a function or set of functions. The term engine as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/ output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Processor 202 can be any programmable device that accepts digital data as input, is configured to process the input according to instructions or algorithms, and provides results as outputs. In an embodiment, processor 202 can be a central processing unit (CPU) configured to carry out the instructions of a computer program. Processor 202 is therefore configured to perform at least basic arithmetical, logical, and input/output operations. Processor 202 can be a microprocessor, a controller, a digital signal processor (DSP), ASIC, FPGA, discrete logic circuitry, or the like.

Memory 204 can comprise volatile or non-volatile memory as required by the coupled processor 202 to not only provide space to execute the instructions or algorithms, but to provide the space to store the instructions themselves. Memory 204 can include program instructions that, when executed by processor 202, cause the systems to implemented the various functions described herein. Memory 204 can include any volatile, non-volatile, magnetic, optical, or electrical media, such as a random access memory (RAM), read-only memory (ROM), non-volatile RAM (NVRAM), electrically-erasable programmable ROM (EEPROM), flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of embodiments.

Measurement engine 206 is configured to operate on one or more signals of interest, according to a signal classification algorithm. For example, measurement engine 206 can include or otherwise utilize a sensor such as a local field potential sensor, chemical sensor, and/or movement sensor in coordination with a signal classification algorithm to determine characteristics related to one or more signals of interest measured by the sensor. In an embodiment, the sensor senses a patient parameter, and values of the patient parameter can be determined (such as by processor 202) based on the signal generated by the sensor as a function of the patient parameter.

Actuation engine 208 is configured with at least one control parameter and a control policy to generate a stimulation waveform adjustment to the control parameter such as amplitude, pulse width, rate, location, electrode configuration and field shape, pattern, schedule or some combination therein. Accordingly, actuation engine 208 can include or otherwise utilize stimulation contacts, leads, electrodes, and so on, of IMD 102.

Reconfiguration engine 210 is configured to dynamically adjust one or more components of measurement engine 206 and/or actuation engine 208. In an embodiment, reconfiguration engine 210 can utilize internal performance characteristics of the control system (e.g. dwell time/entropy in a particular state, actuator saturation, actuator oscillation/stability, etc.), or external inputs provided by another subsystem (e.g. poor symptom control, undesired side effects, etc.) to adjust one or more components of measurement engine 206 and/or actuation engine 208.

Accordingly, the components of system 200 can be implemented wholly as part of or internal to IMD 102. In other embodiments, the components of system 200 can be implemented wholly or partially external to IMD 102 such that a governor overseer such as external device 106, 106a, or 106b can update the functionality of IMD 102. In other embodiments, the components of system 200 can be implemented as a highly distributed system over a cloud and/or server network.

Figure 4:
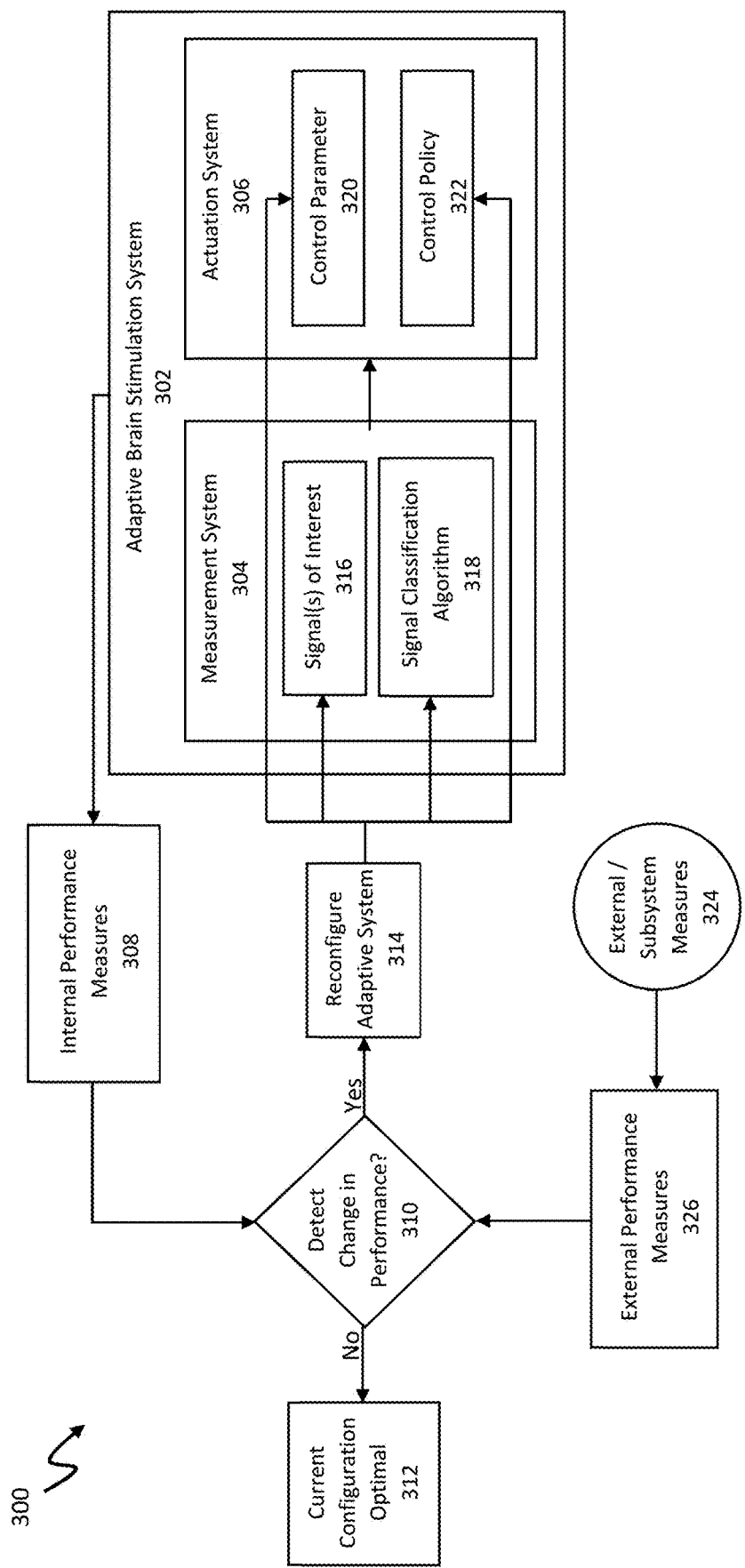
FIG. 4 is a combination block diagram and flowchart of a system that provides robust adaptive brain stimulation, according to an embodiment.

Referring to FIG. 4, a combination block diagram and flowchart of a system 300 that provides robust adaptive brain stimulation is depicted, according to an embodiment. System 300 generally comprises an adaptive brain stimulation system 302 and components to reconfigure adaptive brain stimulation system 302.

More particularly, system 300 is configured for reconfiguration of adaptive brain stimulation system 302, which itself can adapt. Adaptive brain stimulation system 302 generally comprises a measurement system (or subsystem) 304 and an actuation system (or subsystem) 306. Though not shown, it is readily understood by one of ordinary skill in the art that actuation system 302 can adapt or regulate the stimulation delivered to the brain, for example, by getting physiological feedback and adjusting the therapy based on the physiological feedback compared to a threshold value.

In an embodiment, components depicted outside of adaptive brain stimulation system 302 can be included in a reconfiguration subsystem (not labelled for ease of illustration). The reconfiguration of adaptive brain stimulation system 302 is accordingly not mere adjustments of therapy based on a physiological feedback comparison against a threshold value.

Rather, in operation, at 308, system 300 senses, obtains, or otherwise retrieves at least one internal performance measure of adaptive brain stimulation system 302.

At 310, an analysis or evaluation is conducted as to whether there is a change in performance of adaptive brain stimulation system 302 based on the inputted at least one internal performance measure.

At 312, based on the analysis at 310, there is no change detected in performance of adaptive brain stimulation system 302 and system 300 is determined to be optimal.

However, at 314, if a change in performance of adaptive brain stimulation system 302 is detected, adaptive brain stimulation system 302 can be reconfigured. In an embodiment, as illustrated, a change to one or more signals of interest 316, a signal classification algorithm 318, a control parameter 320, and/or a control policy 322 can be made.

In an embodiment, one or more signals of interest 316 can include patient LFP signals (frequency and amplitude), patient kinematic signals (e.g. wearable sensor rotational rate), and/or patient symptom/side effect sensor signals (e.g. visual sensor classifying patient movement).

For example, for electrophysiological local field potentials, embodiments can include the variation of the signal over time, or specific features (bursts, spikes). Embodiments can further include derived properties of the signal, such as power in a specific frequency band (beta power). Embodiments can further include changes in either time or power behavior (bursting in beta). Embodiment can include relationships between two LFP signals (coherence, synchrony, dysynchrony).

In another example, patient kinematic signals can be wearable measures of movement, movement quality, symptom specific measures like tremor detection, overall activity/rest measures, gait or gait quality, or events such as falls.

In another example, patient symptoms can be reported by the patient or can be detected by external systems (e.g. video analysis). Patient symptoms can further include items like medication markers (reported or detected by a smart pill box).

In further examples, one or more signals of interest 316 can further include chemical sensors of physiological markers (neurotransmitters, metabolic byproducts) or of drug levels in the body (l-dopa levels, or markers of l-dopa breakdown), cardiac heart rate, respiration, sleep metrics, blood sugar, and/or temperature.

In an embodiment, signal classification algorithm 318 can include any algorithm used to provide a clinical context to signal of interest(s) 316 either in a continuous mode or discrete mode. For example, in a continuous mode: a real time error in a signal of interest compared to a desired target value. In a discrete mode: classifying the signal of interest into predefined bins of values such as (Low/Middle/High), etc. In another example, signal classification algorithm 318 can include discrete measures such as (above/within/below).

In another embodiment, signal classification algorithm 318 can include derived measures like variance or rate of change, rising/falling, stability or trend metrics.

In another embodiment, embodiments of signal classification algorithm 318 can include or implement event or state detection; for example (pre seizure/in seizure/post seizure), (rigid/dyskinetic), (sleep/wake).

In an embodiment, control parameter 320 can include any parameter related to selection of one or more signal of interest 316.

In an embodiment, control policy 322 can include any mathematical description that relates control parameters and the output of the classification algorithm to the actuator response. For example, an increase/decrease in stimulation output in response to a decrease/increase in a particular, or combination of, control parameter(s) and their classified output. Such examples can be dual threshold single threshold or single threshold inverse.

In embodiments, control policy 322 can be utilized for pattern switching. As described herein, embodiments are configured to anticipate patterns of stimulation that might be delivered at the same amplitude but which are designed in their pulse sequences to have a greater or lesser desynchronizing effect on SOI. Accordingly, pattern switching is utilized as control policy 322 output and/or target for adaptation.

In an embodiment, similar to the aforementioned determinations based on internal performance measures, external/subsystem measures can be obtained at 324. External subsystem measures can be input to 310 for analysis or evaluation as to whether there is a change in performance of adaptive brain stimulation system 302. Evaluations using internal performance measures 308 can be separate or discrete from evaluations using external/subsystem measures 324. In other embodiments, evaluations can utilize both internal performance measures 308 and external/subsystem measures 324 to determine optimal or suboptimal configurations.

Figure 5:
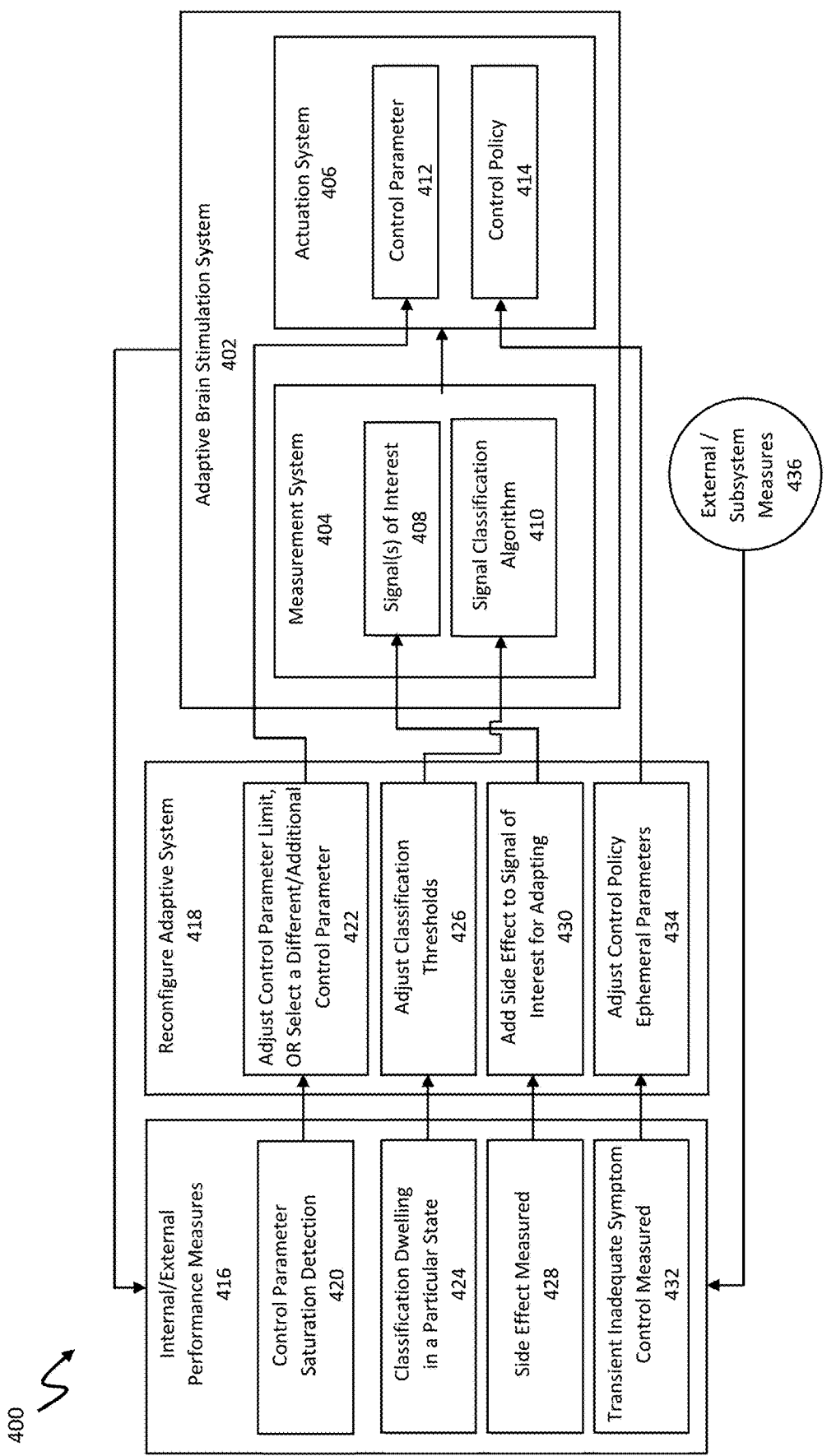
FIG. 5 is a combination block diagram and flowchart of a system that provides robust adaptive brain stimulation, according to an embodiment.

Referring to FIG. 5, a combination block diagram and flowchart of a system 400 that provides robust adaptive brain stimulation is depicted, according to an embodiment. Similar to FIG. 4, system 400 is configured for reconfiguration of adaptive brain stimulation system 402. System 400 generally comprises an adaptive brain stimulation system 402 and components to reconfigure adaptive brain stimulation system 402.

More particularly, system 400 is configured for reconfiguration of adaptive brain stimulation system 402, which itself can adapt. Adaptive brain stimulation system 402 generally comprises a measurement system (or subsystem) 404 and an actuation system (or subsystem) 406. In an embodiment, components depicted outside of adaptive brain stimulation system 402 can be included in a reconfiguration subsystem.

In an embodiment, measurement system 404 generally comprises one or more signals of interest 408 and a signal classification algorithm 410. In an embodiment, actuation system 406 generally comprises one or more control parameters 412 and a control policy 414.

In operation, reconfiguration subsystem can utilize performance measures 416 to reconfigure 418 adaptive brain stimulation system 402.

In an embodiment, reconfigure at 418 includes adding a new state to an existing set of control states. For example, when it is determined that the existing control states/thresholds are not able to account for newly arising conditions, a new state can be added. As an example, a patient initially with two states (On/Off PD symptoms) might develop a third state over time (On with dyskinesias) that is not simply an extension of the On state thresholds, but requires separate management.

The examples of performance measures and reconfiguration provided in FIG. 5 are provided by way of example only, and are in no way limiting.

In an embodiment, internal performance measures are determined based on inputs from adaptive brain stimulation system 402 and analyzed at 416. In an embodiment, external performance measures 436 are determined based on inputs from external to adaptive brain stimulation system 402 and analyzed at 416.

At 420, saturation of a control parameter is detected. Accordingly, at 422, an adjustment to the control parameter limit or selection of a different or additional control parameter is made. As illustrated, such adjustments reconfigure control parameter 412.

At 424, classification dwelling in a particular state is detected at 424. In embodiments, the states can be predefined or dynamically defined based on the therapy. Accordingly, at 426, an adjustment to the classification thresholds 426 is made. As illustrated, such adjustments reconfigure signal classification algorithm 410.

At 428, a side effect is measured. Accordingly, at 430, the side effect can be added to signal of interest 408. As illustrated, such adjustments reconfigure signal of interest 408.

At 432, a transient inadequate symptom control is measured. Accordingly, at 434, control policy ephemeral parameters are adjusted. As illustrated, such adjustments reconfigure control policy 414.

Additional embodiments are described herein with respect to FIGS. 6-9. The systems depicted and described by these figures can be implemented by the components of FIGS. 1-5, as will readily be understood by one of ordinary skill in the art.

Figure 6:
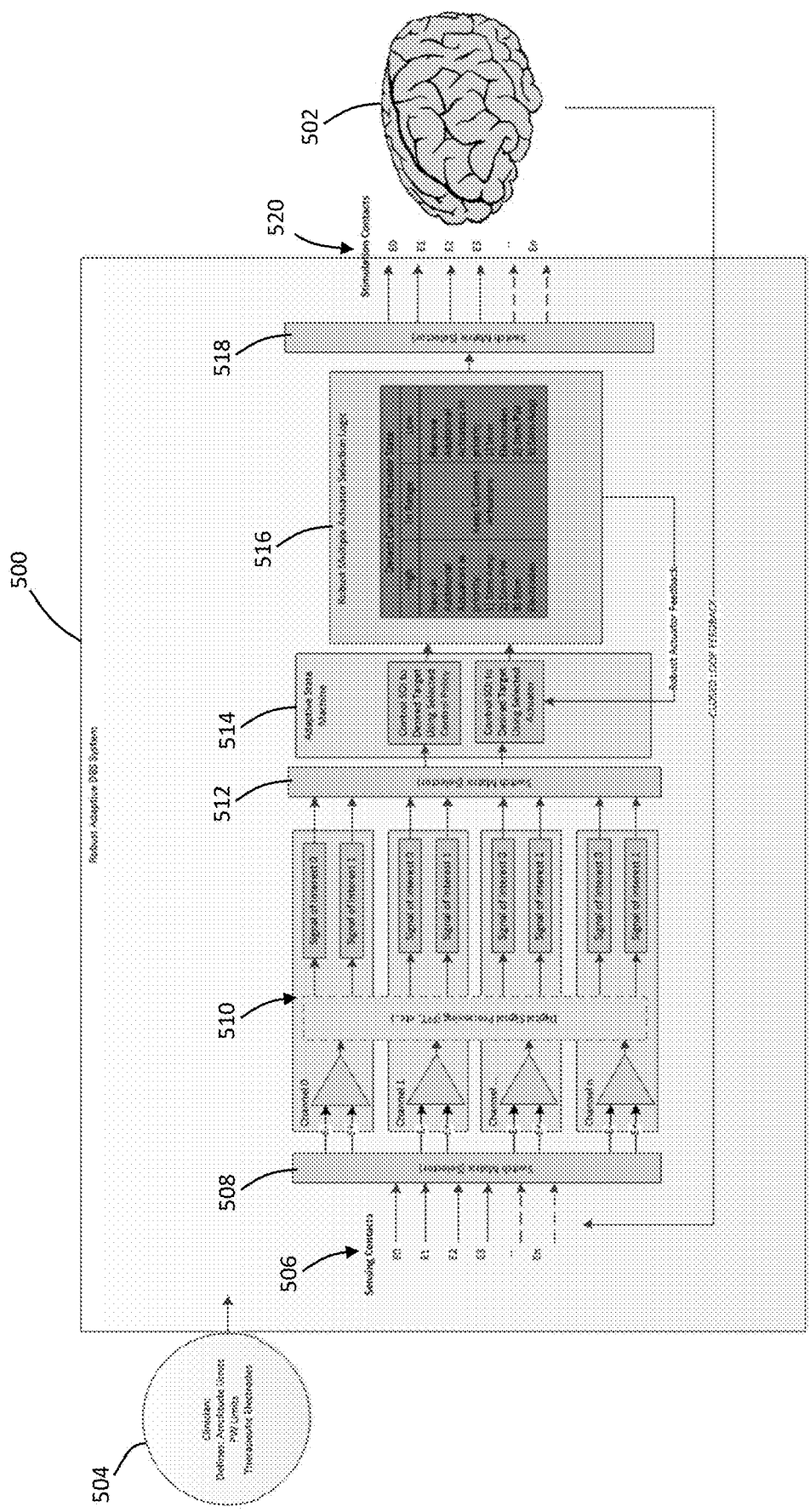
FIG. 6 is a block diagram of a system that provides robust adaptive brain stimulation in view of multiple actuators, according to an embodiment.

Referring to FIG. 6, a block diagram of a system 500 that provides robust adaptive brain stimulation in view of multiple actuators to a patient brain 502 is depicted, according to an embodiment. System 500 is configured to be robust to control actuator saturation.

In an embodiment, system 500 comprises a plurality of sensing contacts 506, a first switch matrix 508, a plurality of signals of interest 510 generated according to a plurality of channels and a digital signal processing, a second switch matrix 512, an adaptive state machine 514, actuator selector logic 516, a third switch matrix 518, and a plurality of stimulation contacts 520.

In operation, at least one of the plurality of sensing contacts 506 are input to first switch matrix 508, which is configured to down-select one or more of the plurality of sensing contacts 506. Based on the selection, inputs to the respective channels is made, and subsequent signal processing is conducted to generate the plurality of signals of interest 510. At least one of the signals of interest 510 are input to second switch matrix 512, which is configured to down-select inputs to adaptive state machine 514.

Adaptive state machine 514 is configured to control at least one signal of interest to a desired target using a selected control policy. In embodiments, adaptive state machine is further configured to control at least one signal of interest to a desired target using a selected actuator.

From adaptive state machine 514, inputs to actuator selector logic 516 are made. Actuator selector logic 516 is configured to detect a current actuator state and classify the actuator as "high", "in range", or "low". Based on the actuator classification, an input to third switch matrix 518 is made. Third switch matrix 518 is configured to select among the plurality of stimulation contacts 520 for interaction with patient brain 502.

In an embodiment, a new adaptive state machine can be swapped in entirely. For example, based on detected performance changes, adaptive state machine 514 can include a set of logic blocks, wherein the actuator feedback can attempt to optimize within a first adaptive state machine, but then switch to an entirely different second adaptive state machine when it becomes clear a new state has been entered. As an example, the control policy for preventing a seizure might look so different to that for responding to/aborting a seizure that it is better thought of as a whole new regime.

In robust adaptive operation, a clinician defines the operating space as an input 504 to system 500. In an embodiment, the clinician defines not only a clinically relevant stimulation amplitude operating space, but also stimulation pulse width operating space, and stimulation electrodes that are therapeutic. In an embodiment, safety limits such as those defined by the clinician are important to systems operating on the brain over general control system theory.

System 500 controls the signal of interest using a defined control policy (e.g. dual threshold, single threshold, single threshold inverse, etc.). Further, embodiments also monitor the state of the actuators that are in use. If a particular actuator becomes saturated in the upper limit of that actuators operating space, another actuator is recruited for use, as defined by the clinician's priority of actuation preference (e.g. from input 504). Likewise, if additional actuators have been recruited, and at a later point in time the additional actuators saturate in the lower limit of their operating space, the saturated actuators are removed from the actuation system.

In an embodiment, when actuator selector logic 516 determines an actuator state to be high, additional actuators can be recruited in a priority order, such as that illustrated—increase stimulation amplitude, stimulation pulse width, then stimulation electrodes. In an embodiment, when actuator selector logic 516 determines an actuator state to be low (in which the stimulation actuators likely need to be turned down), actuators are removed in a priority order, such as that illustrated—stimulation electrodes, stimulation pulse width, then stimulation amplitude. When actuator selector logic 516 determines an actuator state to be in range, no actuators are added or removed. As depicted, actuator feedback can thus be input back to adaptive state machine 514. Accordingly, robustness comes from recruiting or unrecruiting additional actuators. In embodiments, a clinician can choose the order of relative addition or removal, or the relative order can be predefined.

Figure 7:
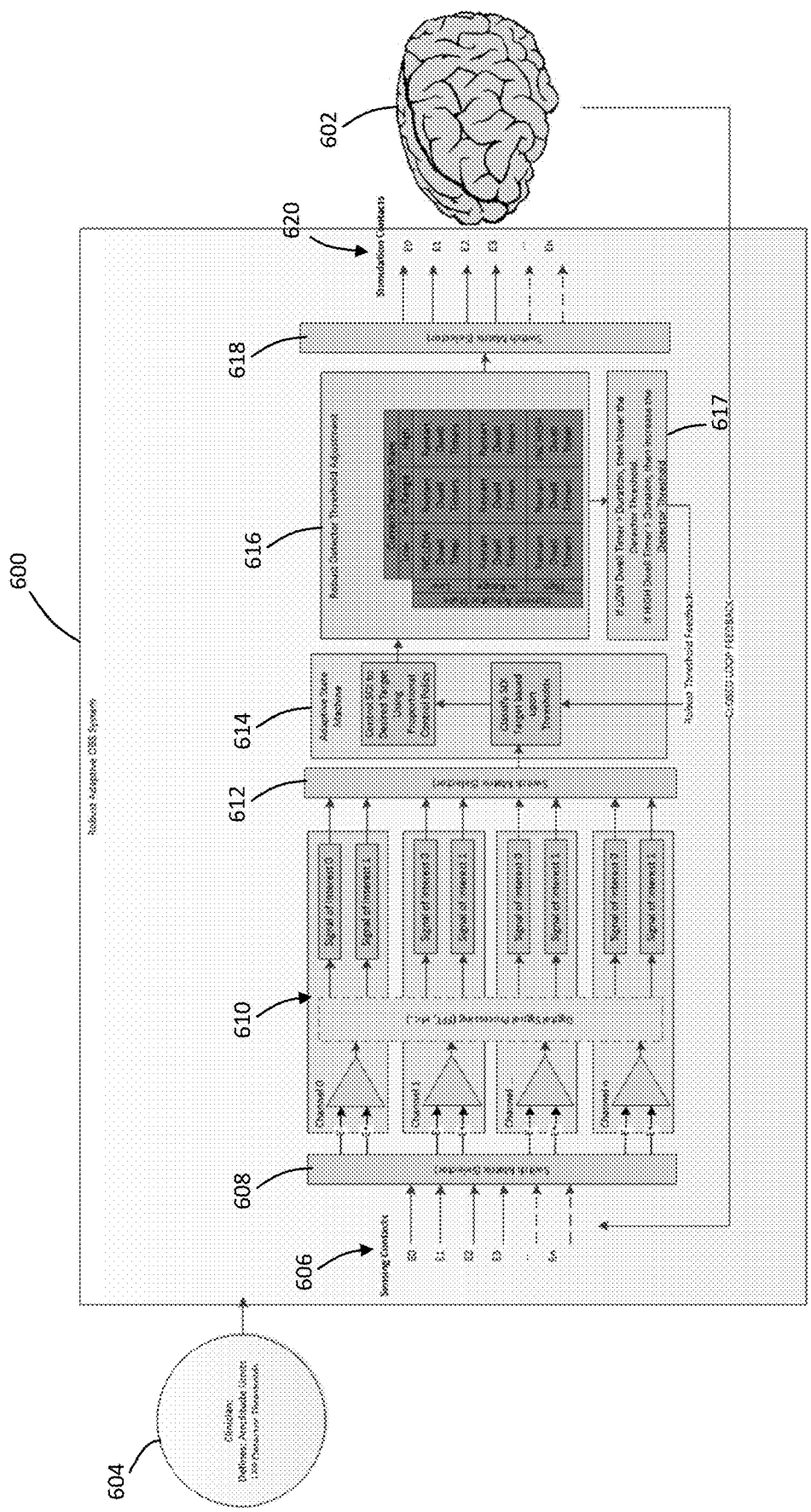
FIG. 7 is a block diagram of a system that provides robust adaptive brain stimulation in view of dwell time, according to an embodiment.

Referring to FIG. 7, a block diagram of a system 600 that provides robust adaptive brain stimulation in view of dwell time to a patient brain 602 is depicted, according to an embodiment.

In an embodiment, system 600 can have substantially similar components to system 500, which are not described again here for conciseness. For example, system 600 can operate on clinician input 604 and comprises a plurality of sensing contacts 606, a first switch matrix 508, a plurality of signals of interest 610 generated according to a plurality of channels and a digital signal processing, a second switch matrix 612, an adaptive state machine 614, a third switch matrix 618, and a plurality of stimulation contacts 620.

As depicted, system 600 can further include detector threshold adjustment logic 616 and 617.

As further depicted, adaptive state machine 614 is configured to classify a signal of interest target based upon thresholds defined in threshold adjustment logic 616 and 617. Adaptive state machine 614 is further configured to control a signal of interest using a proportional control policy. As depicted, threshold feedback can thus be input back to adaptive state machine 614.

In robust adaptive operation, system 600 is robust to SOI thresholds changing over time, or improperly configured to begin with. The clinician defines (e.g. input 604) the stimulation amplitude limits for a proportional control policy. The clinician also defines a signal of interest (SOI) threshold upon which system 600 acts. In an embodiment, system 600 assumes that the clinician-defined stimulation operating space is a clinical constraint, and that system 600 should be adapting stimulation within this envelope, but isn't adapting.

In an embodiment, one or more timers are utilized; for example, a timer that tracks when the controller stops adjusting stimulation due to SOI classification being unchanged. The timer can slowly increment the detector classification of the signal of interest, until the underlying SOI is classified such that stimulation will adapt. Such operation is effective for both over-classified and under-classified signals of interest.

More particularly, referring to threshold adjustment logic 616, a grid of current actuator state against current detector state is depicted for dwell durations "low", "in range", and "high". Corresponding dwell timer operation is illustrated based on the actuator and detector states. The grid accordingly operates on the respective timers based on the times spent above or below the thresholds, in comparison to other inputs.

In an embodiment, for a proportional controller, a low detector input would require low actuation, and a high detector input would require high actuation such that the timers in the grid increment only when in this low/low state or high/high state.

Accordingly, at 617, if a low dwell timer is greater than a defined duration, then the detector threshold is lowered. If a high dwell timer is greater than a defined duration, then the detector threshold is increased. Of course, in certain embodiments, modes can be implemented such that the aforementioned behaviors are overridden or modified. For instance, if it is determined that a patient is sleeping, longer dwell times can be acceptable without adapting thresholds, and so the system might be slowed or paused until a new state is detected.

For example, if a controller stops adjusting stimulation for a long period of time (e.g. a defined duration), the threshold should be adjusted. A lack of action therefore causes threshold adjustment. Traditionally, where adaptive systems are SOI tracking, the actuation system control policy adapts based on crossing a threshold. Embodiments of robust adaptive system 600 are configured to further adjust the thresholds themselves based on how long the SOI has been stuck in a particular state.

As depicted, if the current detector state is low and the actuator state is low, the dwell timer will be increased because the patient is in a low brain state. Further, assuming the respective state does change state, if the low detection timer gets too long, the detection threshold can be lowered such that the threshold is not "low" anymore. For example, if the stimulation cannot be turned down enough to go lower, then threshold set by clinician "low" is no longer low enough. Accordingly, the signal previously classified as "low" is more like a normal signal. As an example, a patient may be on a new medication regime that globally suppresses all signals. Accordingly, normal and abnormal levels are shifted such that the old thresholds are no longer useful.

Figure 8:
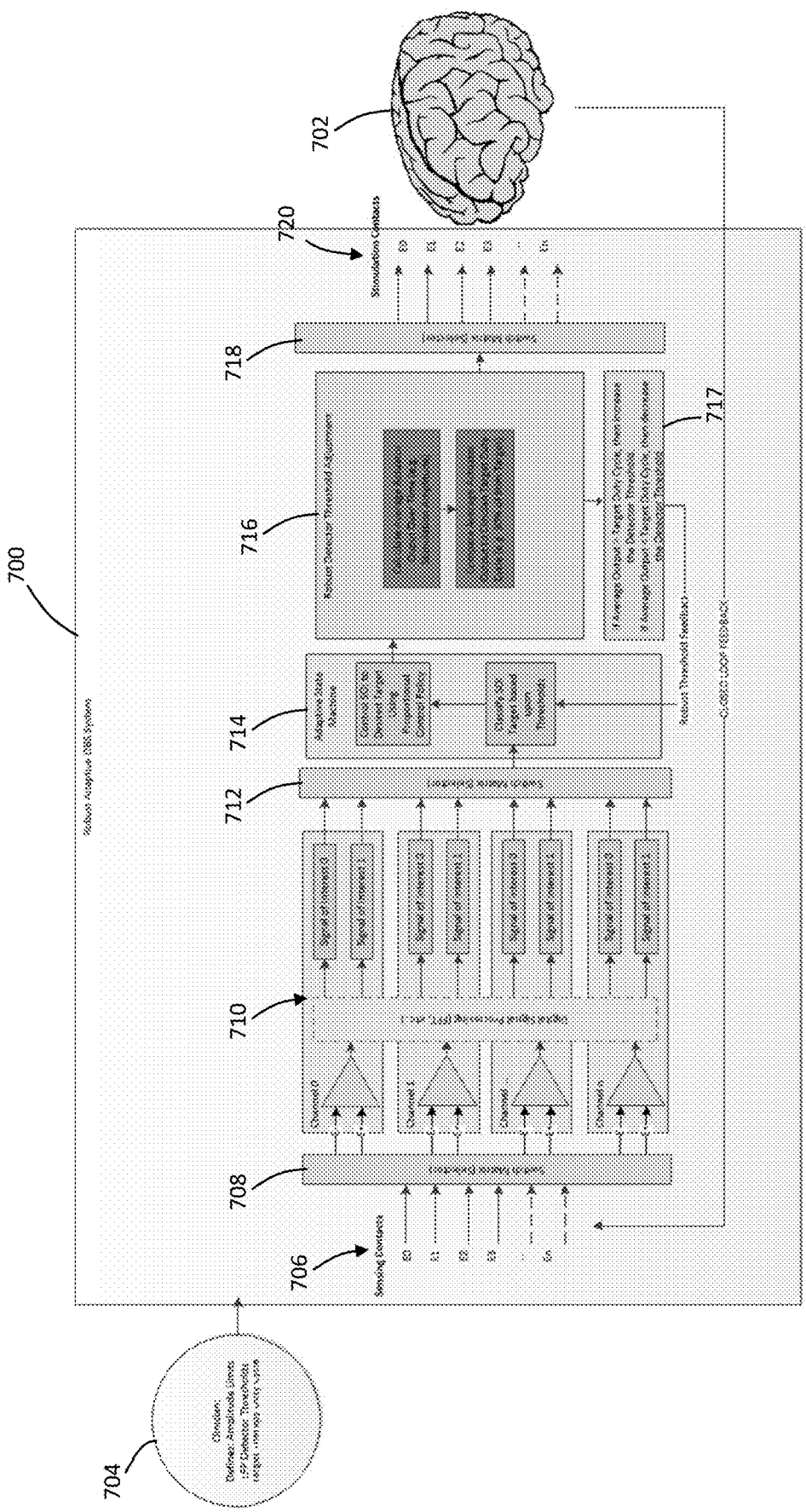
FIG. 8 is a block diagram of a system that provides robust adaptive brain stimulation in view of therapy duty cycle, according to an embodiment.
Figure 9:
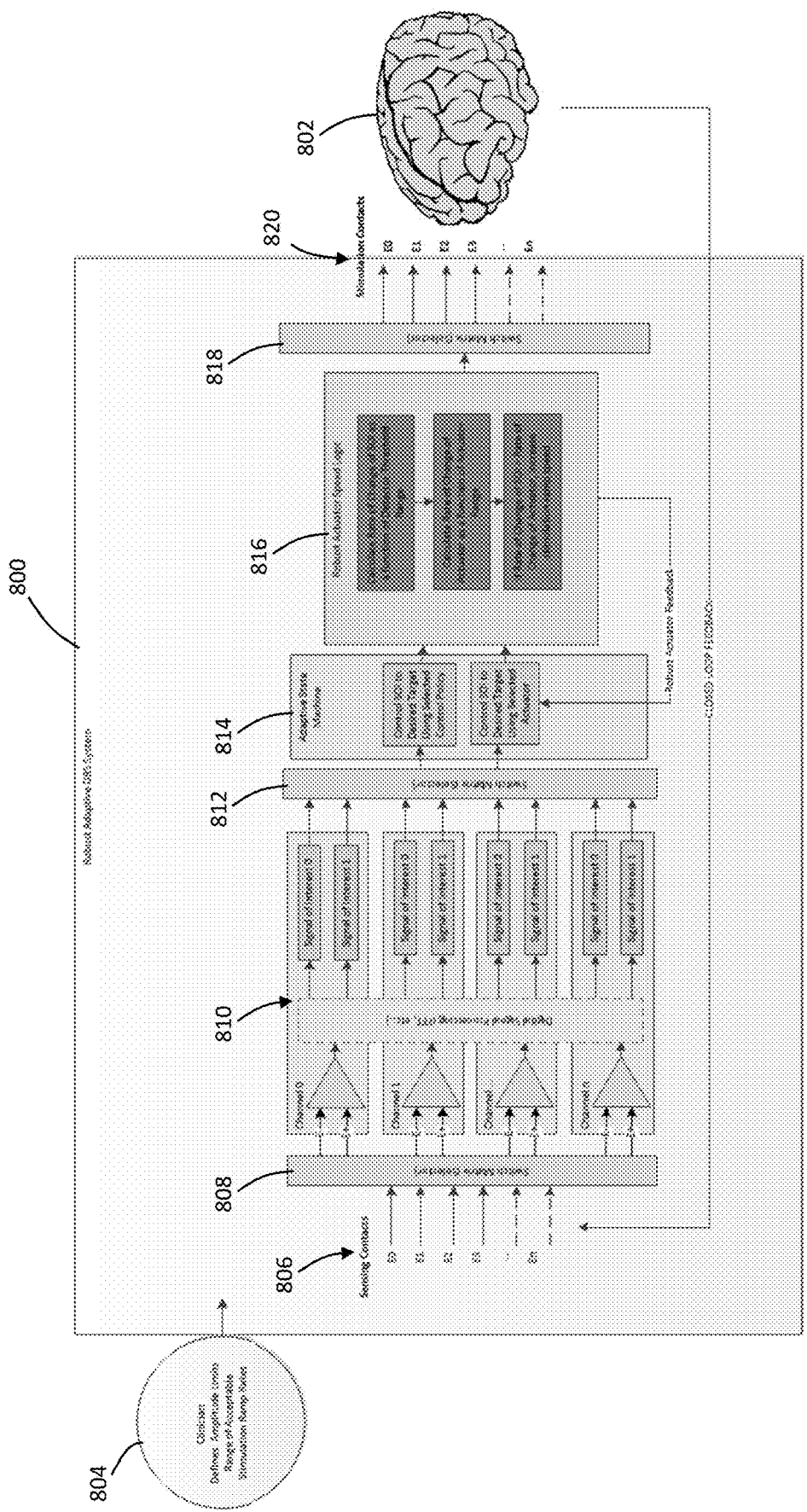
FIG. 9 is a block diagram of a system that provides robust adaptive brain stimulation in view of actuation speed, according to an embodiment.

Referring to FIG. 8, a block diagram of a system 700 that provides robust adaptive brain stimulation in view of therapy duty cycle to a patient brain 702 is depicted, according to an embodiment.

In an embodiment, system 700 can have substantially similar components to systems 500 and 600, which are not described again here for conciseness. For example, system 700 can operate on clinician input 704 and comprises a plurality of sensing contacts 706, a first switch matrix 708, a plurality of signals of interest 710 generated according to a plurality of channels and a digital signal processing, a second switch matrix 712, an adaptive state machine 714, a third switch matrix 718, and a plurality of stimulation contacts 720.

As depicted, system 700 can further include detector threshold adjustment logic 716 and 717.

Similar to system 600, adaptive state machine 714 is configured to classify a signal of interest target based upon thresholds defined in threshold adjustment logic 716 and 717. Adaptive state machine 714 is further configured to control a signal of interest using a proportional control policy. As depicted, threshold feedback can thus be input back to adaptive state machine 714.

In robust adaptive operation, system 700 is robust to SOI thresholds changing over time, or improperly configured to begin with. The clinician defines (e.g. input 704) the stimulation amplitude limits for a proportional control policy. The clinician also defines a signal of interest (SOI) threshold upon which system 700 acts. In an embodiment, system 700 assumes that the clinician-defined stimulation operating space is a clinical constraint, and that system 700 should be adapting stimulation within this envelope, but isn't adapting.

In embodiments, as part of input 704, the clinician also defines a target therapy duty cycle. For example, if the clinician would like the patient to, on average, be receiving the full stimulation amplitude 50% of the time (when adaptive therapy is running, e.g.), embodiments track the average stimulation amplitude delivered. Alternately, a target therapy duty cycle can allow selection between stimulation waveform patterns delivering more or less energy, or designed for higher or lower impact on the SOI. A detector classification of the signal of interest is then slowly incremented, until the underlying SOI is classified such that stimulation will adapt at the target duty cycle provided by the clinician. Such operation is effective for both over-classified and under-classified signals of interest.

More particularly, referring to threshold adjustment logic 716, embodiments are configured to calculate an average actuator output over time (e.g. a stimulation amplitude). Embodiments are further configured to compare the average actuator output to a clinician target duty cycle. In an embodiment, a target duty cycle can be "50% of the stimulation target". Other target duty cycles are of course considered.

Accordingly, at 717, if the average actuator output is greater than the target duty cycle, then the detector threshold is increased. If the average actuator output is less than the target duty cycle, then the detector threshold is decreased. As depicted, threshold feedback can thus be input back to adaptive state machine 714.

In embodiments, by using a metric that can be constantly calculated or calculated at a particular rate, the therapy can be appropriately reclassified. For example, if a therapy is not tracking with clinician-defined parameter(s), the SOI is incorrect because the patient's disease has changed, the patient is taking more medication or less medication, etc., the SOI can be can reclassified based on how much stimulation, for example, is turned on or off Referring to FIG. 9, a block diagram of a system 800 that provides robust adaptive brain stimulation in view of actuation speed to a patient brain 802 is depicted, according to an embodiment.

In an embodiment, system 800 can have substantially similar components to systems 500, 600, and 700, which are not described again here for conciseness. For example, system 800 can operate on clinician input 804 and comprises a plurality of sensing contacts 806, a first switch matrix 808, a plurality of signals of interest 810 generated according to a plurality of channels and a digital signal processing, a second switch matrix 812, an adaptive state machine 814, a third switch matrix 818, and a plurality of stimulation contacts 820.

As depicted, system 800 can further include actuator speed logic 816.

As further depicted, adaptive state machine 814 is configured to control a signal of interest to a desired target a selected actuator based on actuator speed logic 816. Adaptive state machine 814 is further configured to control a signal of interest using a selected control policy. Accordingly, actuator feedback can thus be input back to adaptive state machine 814.

In robust adaptive operation, system 800 is robust to changing physiologic response times. That is, if the physiologic response becomes faster than the actuation system, system 800 increases the actuation system speed. In this example, this is achieved by adjusting the stimulation ramp rate to go faster if the SOI is changing more rapidly. The stimulation ramp rates can be within a bounded set defined by the clinician (e.g. input 804).

More particularly, referring to actuator speed logic 816, embodiments are configured to calculate a rate of change of an SOI as a function of a detector threshold range. Embodiments are further configured to calculate a rate of change of an actuator as a function of the actuator range. If the rate of change of the SOI is greater than the range of change of the actuator, then the stimulation ramp speed is increased.

Accordingly, it is desirable to be able to actuate system 800 at least as fast as the SOI is changing. Accordingly, in faster physio response embodiments, if the SOI is changing faster than the actuator is able to move, then embodiments can change the rate or ramp speed at which stimulation is increased or decreased.

Embodiments shown herein, particularly with respect to FIGS. 6-9 have various feedback loops. For example, referring to FIG. 6, system 500 includes both a closed loop feedback loop from patient brain 502 to plurality of sensing contacts 506, as well as a robust actuator feedback loop from 516 to 514. As described herein, the robust actuator feedback loop adapts the adaptive closed loop feedback loop (and corresponding operations, where applicable). Accordingly, while the closed loop feedback loop is directed towards shorter-term at-issue therapy, the robust actuator feedback loop is directed towards longer-term therapy effectiveness.

In systems using IMDs, battery and processing usage considerations are often a key issue. In a feature and advantage, robust adaptive therapy as described herein, while potentially utilizing additional processing, battery, and communication resources (e.g. reconfiguration using external embodiments), realizes a net gain in resources due to less therapy output by the IMD.

In an embodiment, a level of detected stimulation can be utilized as an internal performance measure to adapt the systems and methods described herein. For example, traditional systems often have trouble with stimulation artifacts (especially those coming from changes in stimulation level or stimulation ramping) being sensed along with the SOI and potentially corrupting the SOI. In embodiment, a level of detected stimulation artifact can be utilized as an internal performance measure to adapt the stimulation level, rate of change, and/or pattern to minimize any corruption.

For example, an electrical stimulation artifact can be sensed via hardware and/or software. Once detected, the electrical stimulation artifact can be removed from the SOI prior to the SOI being input to the measurement system. In another embodiment, the electrical stimulation artifact can sent without removal in the SOI but instead, handled within the logic of the control parameter and/or control policy in addition to the aforementioned methods to effectively step down the various states in accordance with the electrical stimulation artifact.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An adaptive deep brain stimulation system comprising:
   at least one processor and memory operably coupled to the at least one processor;
   a measurement subsystem including:
      a plurality of sensing contacts, and
      measurement subsystem instructions that, when executed on the at least one processor, cause the processor to implement a first signal classification algorithm using one or more of the plurality of sensing contacts to generate a first plurality of signals of interest;
   an actuation subsystem including:
      a plurality of stimulation contacts, and
      actuation subsystem instructions that, when executed on the at least one processor, cause the processor to provide therapy on one or more of the plurality of stimulation contacts by one or more actuators according to a first control policy and a first control parameter;
   a reconfiguration subsystem including reconfiguration subsystem instructions that, when executed on the at least one processor, cause the processor to:
      determine at least one performance measure related to the measurement subsystem or the actuation subsystem,
      detect a change in performance of the at least one performance measure against a performance threshold,
      based on the detecting:
         generate updated measurement subsystem instructions, wherein the updated measurement subsystem instructions includes a second signal classification algorithm or a second plurality of signals of interest, or generate updated actuation subsystem instructions, wherein the updated actuation subsystem instructions includes a second control policy or a second control parameter, store at least one of the updated measurement subsystem instructions or the updated actuation subsystem instructions in the memory, wherein the updated measurement subsystem instructions or the updated actuation subsystem instructions, when executed on the at least one processor, cause the processor to provide an updated therapy on the one or more of the plurality of stimulation contacts.

2. The adaptive deep brain stimulation system of claim 1, wherein the reconfiguration subsystem is implemented in an implantable medical device (IMD).

3. The adaptive deep brain stimulation system of claim 1, wherein the reconfiguration subsystem is implemented in an external device, wherein the external device is not co-located with an implantable medical device (IMD).

4. The adaptive deep brain stimulation system of claim 1, wherein the at least one performance measure is an actuator state and the performance threshold comprises the actuator state having a high value, a low value, or an in-range value.

5. The adaptive deep brain stimulation system of claim 4, wherein when the actuator state has a high value, the second control policy recruits additional actuators in the priority order: stimulation amplitude, stimulation pulse width, and stimulation electrodes.

6. The adaptive deep brain stimulation system of claim 4, wherein when the actuator state has a low value, the second control policy removes additional actuators in the priority order: stimulation electrodes, stimulation pulse width, and stimulation amplitude.

7. The adaptive deep brain stimulation system of claim 1, wherein the reconfiguration subsystem further includes at least one dwell timer, wherein the at least one performance measure is a dwell time calculated by the at least one dwell timer, and the performance threshold is a duration.

8. The adaptive deep brain stimulation system of claim 7, wherein the at least one dwell timer comprises a low dwell timer and a high dwell timer, each of the low dwell timer and high dwell timer categorized according to:

a current actuator state defined by an actuator state high value, an actuator state low value, or an actuator state in-range value against a current detector state defined by a current detector state low value, a current detector state in-range value, or a current detector state high value.

9. The adaptive deep brain stimulation system of claim 8, wherein the second signal classification algorithm includes lowering a detector threshold when the low dwell timer is greater than a first duration and raising the detector threshold when the high dwell timer is greater than a second duration.

10. The adaptive deep brain stimulation system of claim 1, wherein the at least one performance measure is an average actuator output, and the performance threshold is a target duty cycle.

11. The adaptive deep brain stimulation system of claim 10, wherein the second signal classification algorithm includes increasing a detector threshold when the average actuator output is greater than the target duty cycle and decreasing the detector threshold when the average actuator output is less than the target duty cycle.

12. The adaptive deep brain stimulation system of claim 1, wherein the at least one performance measure is:

a rate of change of at least one of the first plurality of signals of interest as a function of a detector threshold range, and a rate of change of an actuator as a function of an actuator range, wherein the performance threshold whether the rate of change of at least one of the first plurality of signals of interest as a function of a detector threshold range is greater than the rate of change of an actuator as a function of an actuator range.

13. The adaptive deep brain stimulation system of claim 12, wherein the second control policy includes increasing stimulation ramp speed when the performance threshold is satisfied.

14. A method for adapting an adaptive deep brain stimulation system including at least one processor and memory operably coupled to the at least one processor, a measurement subsystem including a plurality of sensing contacts, and measurement subsystem instructions that, when executed on the at least one processor, cause the processor to implement a first signal classification algorithm using one or more of the plurality of sensing contacts to generate a first plurality of signals of interest, and an actuation subsystem including: a plurality of stimulation contacts, and actuation subsystem instructions that, when executed on the at least one processor, cause the processor to provide therapy on one or more of the plurality of stimulation contacts by one or more actuators according to a first control policy and a first control parameter, the method comprising:

determining at least one performance measure related to the measurement subsystem or the actuation subsystem, detecting a change in performance of the at least one performance measure against a performance threshold, based on the detecting:

generating updated measurement subsystem instructions, wherein the updated measurement subsystem instructions includes a second signal classification algorithm or a second plurality of signals of interest, or generating updated actuation subsystem instructions, wherein the updated actuation subsystem instructions includes a second control policy or a second control parameter, storing at least one of the updated measurement subsystem instructions or the updated actuation subsystem instructions in the memory, wherein the updated measurement subsystem instructions or the updated actuation subsystem instructions, when executed on the at least one processor, cause the processor to provide an updated therapy on the one or more of the plurality of stimulation contacts.

15. The method for adapting an adaptive deep brain stimulation system of claim 14, wherein the method is implemented in an implantable medical device (IMD).

16. The method for adapting an adaptive deep brain stimulation system of claim 14, wherein the method is implemented in an external device, wherein the external device is not co-located with an implantable medical device (IMD).

17. The method for adapting an adaptive deep brain stimulation system of claim 14, wherein the at least one performance measure is an actuator state and the performance threshold comprises the actuator state having a high value, a low value, or an in-range value.

18. The method for adapting an adaptive deep brain stimulation system of claim 17, wherein when the actuator state has a high value, the method further comprises:
  recruiting, with the second control policy, additional actuators in the priority order: stimulation amplitude, stimulation pulse width, and stimulation electrodes.

19. The method for adapting an adaptive deep brain stimulation system of claim 17, wherein when the actuator state has a low value, the method further comprises:
  removing, with the second control policy, additional actuators in the priority order: stimulation electrodes, stimulation pulse width, and stimulation amplitude.

20. The method for adapting an adaptive deep brain stimulation system of claim 14, further comprising:
  calculating a dwell time using a dwell timer, wherein the at least one performance measure is the dwell time, and the performance threshold is a duration.

21. The method for adapting an adaptive deep brain stimulation system of claim 20, wherein the at least one dwell timer comprises a low dwell timer and a high dwell timer, each of the low dwell timer and high dwell timer categorized according to:
  a current actuator state defined by an actuator state high value, an actuator state low value, or an actuator state in-range value against a current detector state defined by a current detector state low value, a current detector state in-range value, or a current detector state high value.

22. The method for adapting an adaptive deep brain stimulation system of claim 21, wherein the second signal classification algorithm includes lowering a detector threshold when the low dwell timer is greater than a first duration and raising the detector threshold when the high dwell timer is greater than a second duration.

23. The method for adapting an adaptive deep brain stimulation system of claim 14, wherein the at least one performance measure is an average actuator output, and the performance threshold is a target duty cycle.

24. The method for adapting an adaptive deep brain stimulation system of claim 23, wherein the second signal classification algorithm includes increasing a detector threshold when the average actuator output is greater than the target duty cycle and decreasing the detector threshold when the average actuator output is less than the target duty cycle.

25. The method for adapting an adaptive deep brain stimulation system of claim 14, wherein the at least one performance measure is:
  a rate of change of at least one of the first plurality of signals of interest as a function of a detector threshold range, and
  a rate of change of an actuator as a function of an actuator range, wherein the performance threshold whether the rate of change of at least one of the first plurality of signals of interest as a function of a detector threshold range is greater than the rate of change of an actuator as a function of an actuator range.

26. The method for adapting an adaptive deep brain simulation system of claim 25, wherein the second control policy includes increasing stimulation ramp speed when the performance threshold is satisfied.

* * * * *